(12) United States Patent
Bodkin et al.

(10) Patent No.: US 10,902,947 B2
(45) Date of Patent: Jan. 26, 2021

(54) MAGNETIC RESONANCE IMAGING (MRI) CONTROL

(71) Applicant: KONINKLIJKE PHILIPS N.V., Eindhoven (NL)

(72) Inventors: Joseph Bodkin, Fort Meyers, FL (US); John Cronin, Bonita Springs, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

(21) Appl. No.: 16/063,713

(22) PCT Filed: Dec. 26, 2016

(86) PCT No.: PCT/IB2016/058002
§ 371 (c)(1),
(2) Date: Jun. 19, 2018

(87) PCT Pub. No.: WO2017/115264
PCT Pub. Date: Jul. 6, 2017

(65) Prior Publication Data
US 2020/0286617 A1    Sep. 10, 2020

Related U.S. Application Data

(60) Provisional application No. 62/274,079, filed on Dec. 31, 2015.

(51) Int. Cl.
*G16H 40/40*    (2018.01)
*A61B 5/00*    (2006.01)
(Continued)

(52) U.S. Cl.
CPC .......... *G16H 40/63* (2018.01); *A61B 5/0036* (2018.08); *A61B 5/055* (2013.01); *G16H 40/40* (2018.01)

(58) Field of Classification Search
CPC ...... G16H 40/63; G16H 40/40; A61B 5/0036; A61B 5/055
See application file for complete search history.

(56) References Cited

U.S. PATENT DOCUMENTS 7,835,927 B2    11/2010    Schlotterbeck
8,500,694 B2    8/2013    Susi
(Continued)

FOREIGN PATENT DOCUMENTS

WO    2005101279    10/2005

OTHER PUBLICATIONS

Giraud, et al., "Respiratory Gating for Radiotherapy: Main Technical Aspects and Clinical Benefits", ISRN Pulmonology, vol. 2013, Dec. 31, 2013.
(Continued)

*Primary Examiner* — Santiago Garcia

(57) ABSTRACT

The present disclosure generally relates to systems and methods for providing intelligent control to imaging systems, associated patient machines, or both. In one embodiment, the systems and methods provide automated magnetic resonance imaging (MRI) control. An MRI infusion pump/patient monitor may have a cloud/Internet connection and may transfer a patient's data to a patient network while an MRI with the patient is in progress. The data maybe compared to a historical patient database in the patient network. A pump algorithm may be selected based on multiple factors. Such factors may include patient vitals and electronic medical records. The selected pump algorithm may be used to control the MRI infusion pump.

10 Claims, 10 Drawing Sheets

MRI INFUSION/ PATIENT MONITOR
102

(51) Int. Cl.
*A61B 5/055* (2006.01)
*G16H 40/63* (2018.01)

(56) References Cited

U.S. PATENT DOCUMENTS

| | | | | |
|---|---|---|---|---|
| 9,098,861 | B2* | 8/2015 | Ban | G06Q 30/02 |
| 2006/0137699 | A1* | 6/2006 | Moore | G06Q 50/22 |
| | | | | 705/2 |
| 2007/0239490 | A1* | 10/2007 | Sullivan | G06Q 50/24 |
| | | | | 705/3 |
| 2007/0286331 | A1 | 12/2007 | Keall | |
| 2013/0110547 | A1 | 5/2013 | Englund | |
| 2013/0296711 | A1* | 11/2013 | Curiel | A61B 5/0077 |
| | | | | 600/476 |
| 2014/0257854 | A1* | 9/2014 | Becker | G06F 19/321 |
| | | | | 705/3 |
| 2014/0374476 | A1* | 12/2014 | Ban | G16H 10/65 |
| | | | | 235/375 |
| 2015/0035942 | A1* | 2/2015 | Hampton | A61N 5/1049 |
| | | | | 348/42 |
| 2016/0073962 | A1* | 3/2016 | Yu | A61B 5/1127 |
| | | | | 600/407 |
| 2016/0314367 | A1* | 10/2016 | Chmiel | G06K 9/00885 |
| 2017/0042495 | A1* | 2/2017 | Matsuzaki | A61B 6/037 |

OTHER PUBLICATIONS

Bressan, et al., "Integration of Drug Dosing Data with Physiological Data Streams using a Cloud Computing Paradigm"; 35th Annual International Conference of the IEEE EMBS, Osaka, Japan, Jul. 3-7, 2013.
Liu, et al., "Closed-Loop Coadministration of Propofol and Remifentanil Guided by Bispectral Index", Anesthesia & Analgesia: Mar. 2011—vol. 112—Issue 3—p. 546-557.

* cited by examiner

| PATIENT ID | DATE | TIME | MODEL | TYPE | DRUG | SPO2 % | PULSE | RESPIRATORY RATE | TEMPERATURE | BLOOD PRESSURE | ALGORITHM |
|---|---|---|---|---|---|---|---|---|---|---|---|
| PATIENT.1234 | 8/18/2015 | 9:00 AM | MRIDIUM | 3850 | PROPOFOL | 92 | 50 | 25/MIN | 98.8 | 110/70 | ALGO.1234 |
| PATIENT.5678 | 8/18/2015 | 10:00 AM | MRIDIUM | 3850 | PROPOFOL | 91 | 49 | 24/MIN | 98.5 | 112/72 | ALGO.1234 |
| PATIENT.9012 | 8/18/2015 | 11:00 AM | MRIDIUM | 3850 | PROPOFOL | 92 | 50 | 25/MIN | 98.6 | 111/71 | ALGO.1234 |
| PATIENT.3456 | 8/18/2015 | 12:00 PM | MRIDIUM | 3850 | PROPOFOL | 93 | 48 | 23/MIN | 98.4 | 109/69 | ALGO.1234 |
| PATIENT.7890 | 8/18/2015 | 1:00 PM | MRIDIUM | 3850 | PROPOFOL | 93 | 46 | 20/MIN | 98.2 | 109/69 | ALGO.1234 |
| PATIENT.4321 | 8/18/2015 | 2:00 PM | MRIDIUM | 3850 | PROPOFOL | 92 | 45 | 19/MIN | 98.1 | 108/68 | ALGO.1234 |
| PATIENT.0987 | 8/18/2015 | 3:00 PM | MRIDIUM | 3850 | PROPOFOL | 93 | 45 | 17/MIN | 98 | 107/67 | ALGO.1234 |

| PATIENT ID | DATE | TIME | MODEL | TYPE | DRUG | SPO2 % | PULSE | RESPIRATORY RATE | TEMP | BP | ALGORITHM | ACTIONS | SUGGESTION |
|---|---|---|---|---|---|---|---|---|---|---|---|---|---|
| PATIENT.1 | 8/18/2015 | 9:00 AM | MRIDIUM | 3850 | PROPOFOL | 92 | 50 | 25/MIN | 98.8 | 110/70 | ALGO.1234 | 7 | |
| PATIENT.2 | 8/18/2015 | 10:00 AM | MRIDIUM | 3850 | PROPOFOL | 91 | 49 | 24/MIN | 98.5 | 112/72 | ALGO.4122 | 8 | CHECK PATIENT |
| PATIENT.3 | 8/18/2015 | 11:00 AM | MRIDIUM | 3850 | P2 | 92 | 50 | 25/MIN | 98.6 | 111/71 | ALGO.3188 | 21 | |
| PATIENT.45 | 8/18/2015 | 12:00 PM | MRIDIUM | 3850 | PROPOFOL | 93 | 48 | 23/MIN | 98.4 | 109/69 | ALGO.3199 | 10 | |
| PATIENT.90 | 8/18/2015 | 1:00 PM | MRIDIUM | 3850 | PROPOFOL | 93 | 46 | 20/MIN | 98.2 | 109/69 | ALGO.3199 | 20 | |
| PATIENT.21 | 8/18/2015 | 2:00 PM | MRIDIUM | 3850 | PROPOFOL | 92 | 45 | 19/MIN | 98.1 | 108/68 | ALGO.3199 | 20 | |
| PATIENT.87 | 8/18/2015 | 3:00 PM | MRIDIUM | 3850 | PROPOFOL | 93 | 45 | 17/MIN | 98 | 107/67 | ALGO.3199 | 7 | |

602

ALGO 1234 = IF BP > 110

ALGO 4122 = IF SPO2 < 90

ALGO 3188 = DRUG = P2

ALGO 3199 = IF RR < 17/MIN

ACTION 7 = REDUCE IV RATE BY 10%

ACTION 8 = STOP IV PUMP

ACTION 21 = RATE = 15 M/HR

ACTION 10 = ALERT AT IV PUMP

ACTION 20 = REDUCE IV RATE BY 15%

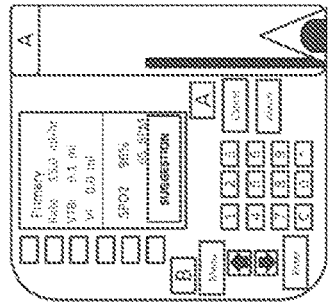

102

FIG. 6 ured States Patent Number US 10,902,947 B2

MAGNETIC RESONANCE IMAGING (MRI) CONTROL

CROSS REFERENCE TO RELATED APPLICATIONS

This application is the U.S. National Phase application under 35 U.S.C. § 371 of International Application No. PCT/IB2016/058002, filed Dec. 26, 2016, published as WO 2017/115264 on Jul. 6, 2017, which claims the benefit of U.S. Provisional Patent Application No. 62/274,079 filed Dec. 31, 2015. These applications are hereby incorporated by reference herein.

BACKGROUND

It is currently difficult to control MRI infusion pumps when the patient is going through the MRI procedure. Some pumps may be controlled by a healthcare professional in a separate room, but because comparative data is not available to the healthcare professional, such control may lead to errors.

There is a need in the art for improved systems and methods for providing intelligent MRI controls.

SUMMARY OF THE CLAIMED INVENTION

The present disclosure generally relates to systems and methods for providing intelligent control to imaging systems, associated patient machines, or both. In one embodiment, the systems and methods provide automated magnetic resonance imaging (MRI) control. An MRI infusion pump/patient monitor may have a cloud/Internet connection and may transfer a patient's data to a patient network while an MRI with the patient is in progress. The data may be compared to a historical patient database in the patient network. A pump algorithm may be selected based on multiple factors. Such factors may include patient vitals and electronic medical records. The selected pump algorithm may be used to control the MRI infusion pump.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings:

FIGS. 5 and 6 illustrate example data that may be stored in a patient network historical database according to some embodiments of the present disclosure.

DETAILED DESCRIPTION

The present invention includes systems and methods for providing intelligent magnetic resonance imaging (MRI) control. An MRI infusion pump/patient monitor may have a cloud/Internet connection and may transfer a patient's data to a patient network while an MRI with the patient is in progress. The data may be compared to a historical patient database in the patient network. A pump algorithm may be selected based on multiple factors. Such factors may include patient vitals and electronic medical records. The selected pump algorithm may be used to control the MRI infusion pump.

Figure 1:
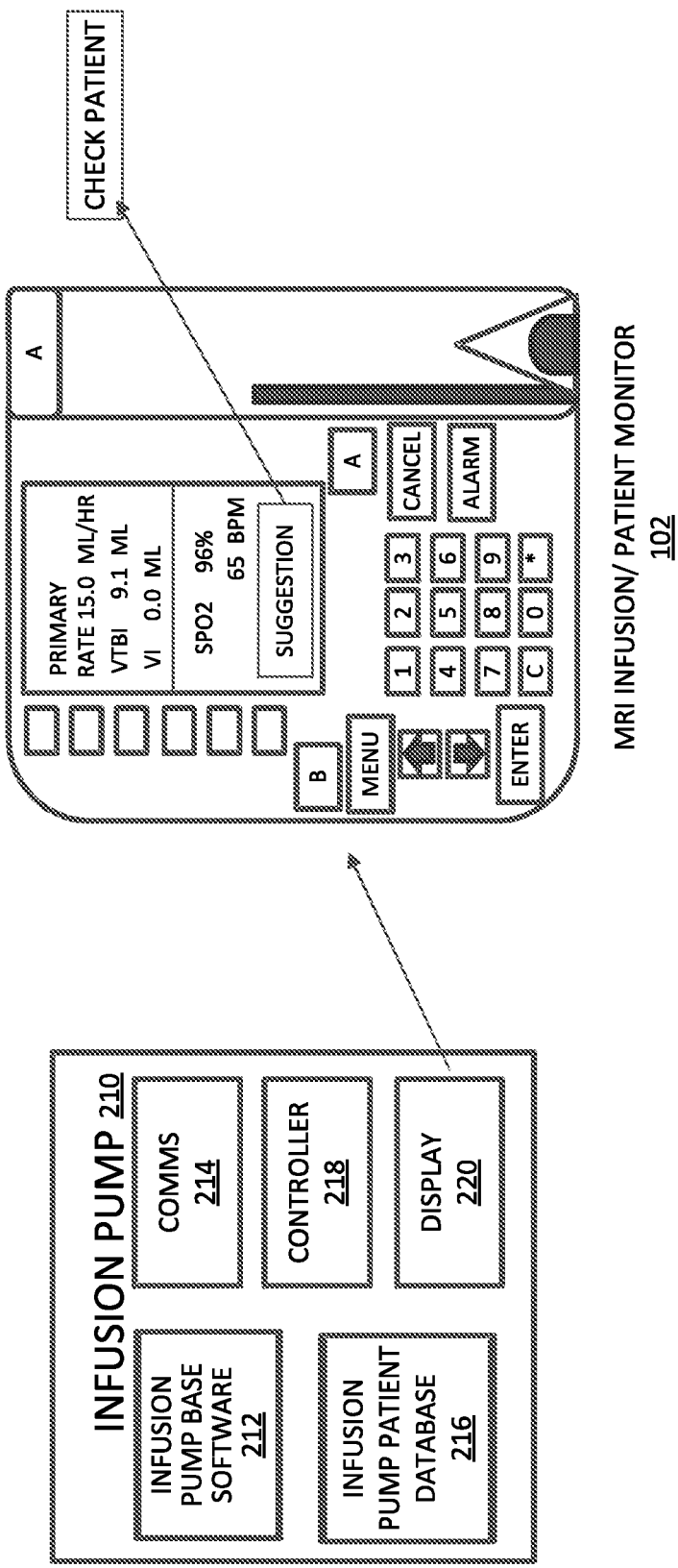
FIG. 1 shows a schematic diagram of an example of system including an exemplary infusion display according to some embodiments of the present disclosure.

FIG. 1 illustrates an environment 100 in which a method for adjusting MRI controls may be implemented. The environment 100 of FIG. 1 may include an MRI infusion and patient monitor 102, a communication network 150 (e.g., the cloud or Internet), an MRI network 152, a patient network 160, and one or more third parties 180. The MRI network 152 may include an IV pump interaction 156. The patient network 160 may include one or more pump algorithms 162, a historical database 164, a third-party application program interface (API), and an MRI interaction 168.

The MRI infusion and patient monitor 102 may collect patient data during an MRI. The MRI and patient monitor 102 may store the collected data into a database. The stored data may be transmitted to the patient network 160. The patient network 160 may be in the cloud. The transmitted data may be compared with data in the historical database 164. The historical database 164 may include patient data collected during one or more other MRI procedures. The historical database may include patient data collected from one or more other patients. An algorithm may be selected from the one or more pump algorithms 162. An algorithm may be selected based on similarities between the transmitted data and historical database data associated with the selected algorithm. An algorithm may be associated with a set of historical database data, for example, and the algorithm may be selected based on similarities between the transmitted data and the set of historical database data. The historical data may include patient vital signs, patient data, and/or electronic medical records. MRI infusion pump controls may be selected for transmission to the MRI infusion and patient monitor 102 using the selected algorithm.

Figure 2:
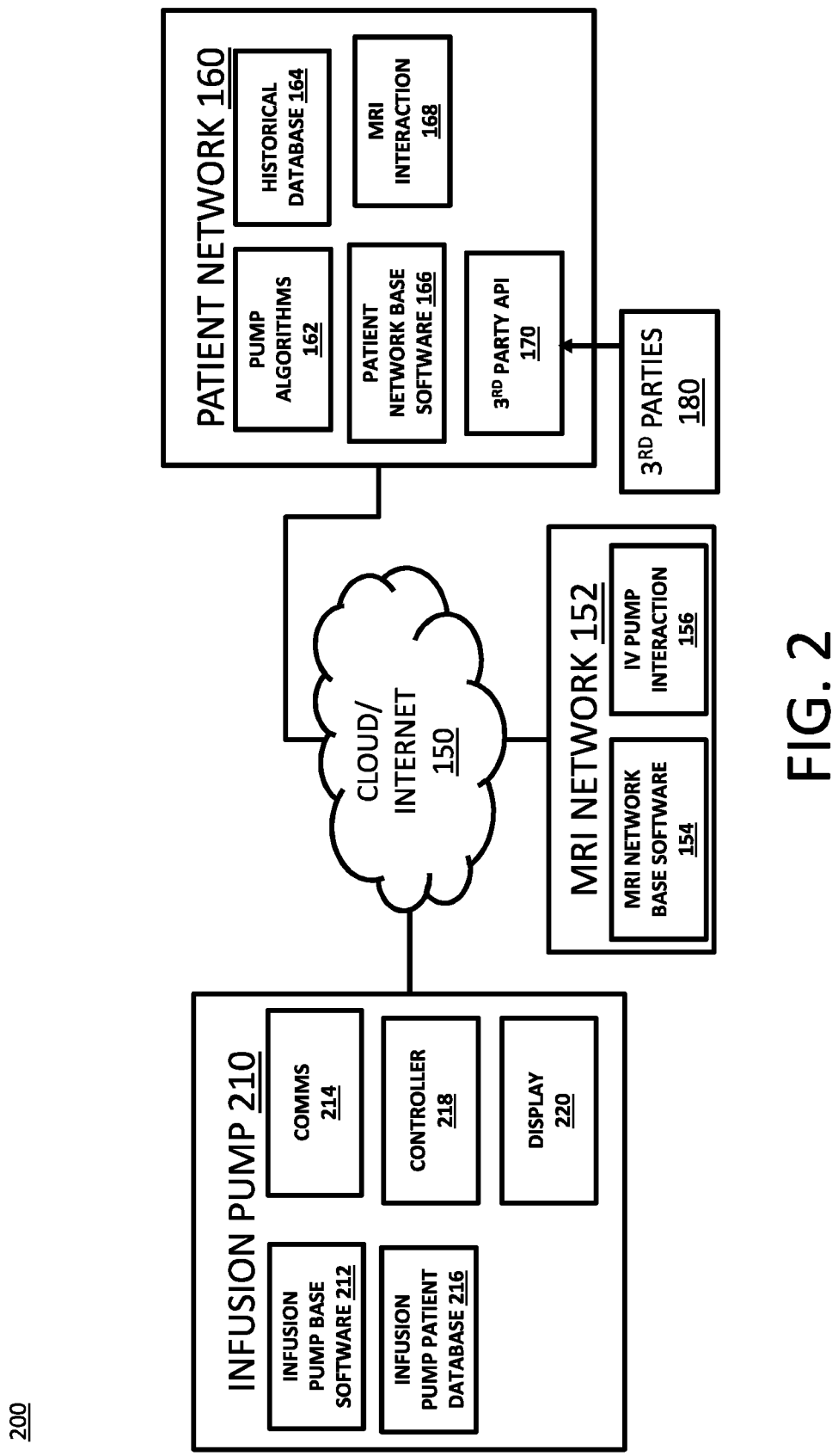
FIG. 2 shows an network environment for an exemplary magnetic resonance imaging (MRI) control system according to some embodiments of the present disclosure.

FIG. 2 illustrates another environment 200 in which a method for adjusting MRI controls may be implemented. The environment 200 of FIG. 2 may include an infusion pump 210, the communication network 150 (e.g., the cloud or Internet), the MRI network 152, the patient network 160, and the one or more third parties 180. The infusion pump 210 may include an infusion pump base software 212, a communication interface 214, an infusion pump patient database 216, a controller 218, and a display 220. The MRI network 152 may include the IV pump interaction 156. The MRI network 152 may also include an MRI network base software 154. The patient network 160 may include the one or more pump algorithms 162, the historical database 164, the third-party application program interface (API), and the MRI interaction 168. The patient network 160 may also include a patient network base software 166. The pump algorithms 162 may be stored in a pump algorithm database (not shown).

The infusion pump 210 may record patient readings during an MRI and store the recorded readings in the database 216. The readings may be transmitted from the infusion pump 210 to the MRI network 152. The readings may be transmitted via the communication network 150 using the communication interface 214. The transmitted readings may be transmitted from the MRI network 152 to the patient network 160. The readings may be compared, using the patient network base software 166, to the historical database 164 after the readings are transmitted to the patient network 160. The patient network base software 166 may identify readings from the database 164 which are similar to the transmitted readings. The patient network base software 166 may identify an algorithm associated with the similar readings. The algorithm may be associated with the similar readings in the database 164. The software 166 may compare the identified algorithm with the pump algorithms 162 to identify a pump algorithm. Actions and/or suggestions associated with the identified pump algorithm may be transmitted to the MRI network 152. The readings transmitted to the patient network 160 are also stored in the historical database 164. The identified algorithm may also be stored and associated with the transmitted readings in the database 164.

The transmitted actions may be transmitted to the controller 218. The transmitted suggestions may be transmitted to the display 220. The infusion pump may use the actions and/or suggestions to control the infusion pump. The infusion pump may also use some but not all of the actions and/or suggestions. A technician controlling the infusion pump, for example, may choose to implement some but not all of the actions and/or suggestions.

The one or more third parties 180 may access the patient network via the third party API 170. The one or more third parties 180 may be researchers and/or manufactures of MRI equipment. The third parties 180 may use the database 164 to improve algorithms and/or improve algorithms.

The patient network 160 may identify, for an infusion pump 210, a model name and/or model type, based on the readings transmitted from the infusion pump 210. The patient network 160 may use the model name and/or model type to select a pump algorithm from the one or more pump algorithms 162.

Figure 3:
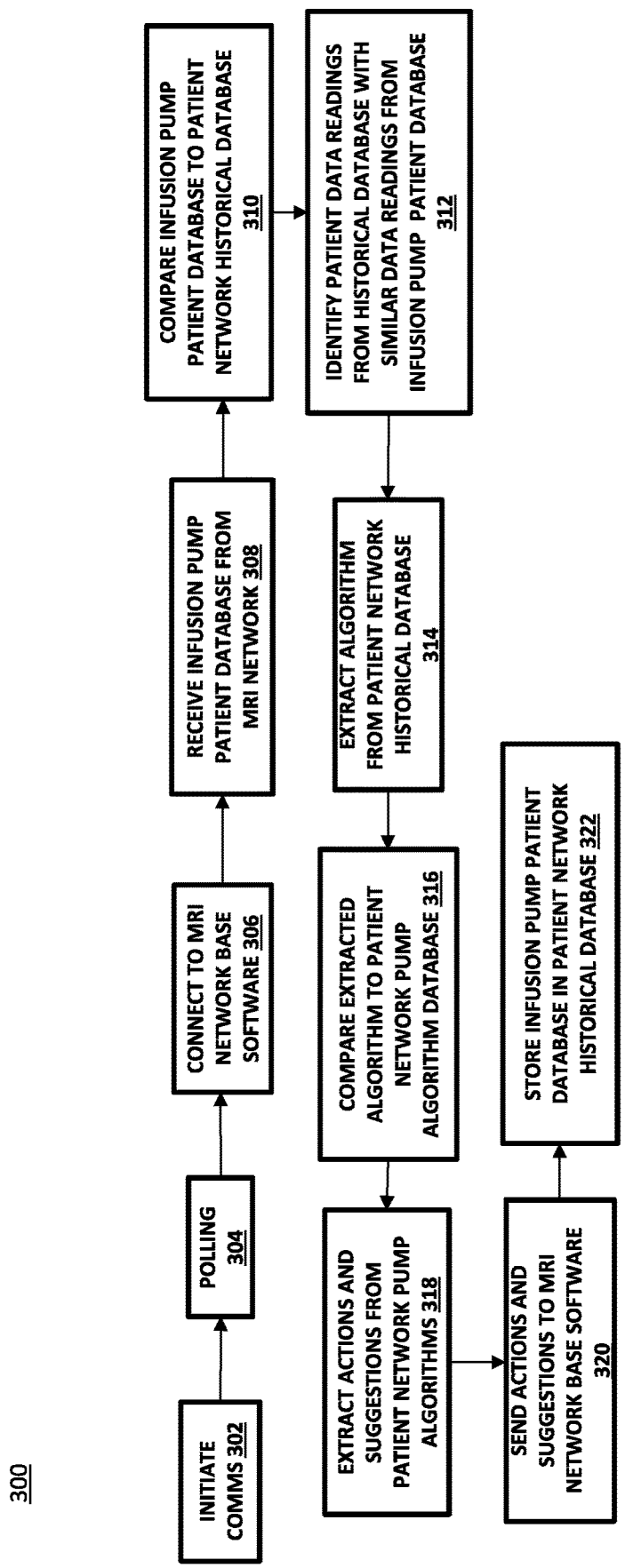
FIG. 3 is a flow diagram illustrating a method for identifying MRI control information according to some embodiments of the present disclosure.

FIG. 3 is a flow diagram illustrating a method 300 for identifying MRI control information. In step 302 of FIG. 3, the patient network base software 166 may initiate communication. The patient network base software 166 may initiate communication through various channels. The patient network base software 166 may initiate communication through a communication interface. The communication interface may be included in the patient network 160. The communication interface may communicate via the communication network 150.

In step 304, the patient network base software 166 may continue polling for a connection with the MRI network 152. The patient network base software 166 may poll for a connection until a connection is established. The patient network base software 166 may poll for a connection when a disconnection occurs between the patient network base software 166 and the MRI network 152.

In step 306, the patient network base software 166 may connect to the MRI network 152. The patient network base software 166 may connect to the MRI network 152 via the communication network 150.

In step 308, the patient network base software 166 may receive, from the MRI network 152, the infusion pump patient database 216. The infusion pump patient database 216 may be provided to the patient network 160 by the MRI network base software 154. The MRI network 152 may provide the infusion pump patient database 216 to the patient network 160 after receiving the database 216 from the infusion pump 210.

In step 310, the patient network base software 166 may compare the received infusion pump patient database 216 with the patient network historical database 164.

In step 312, the patient network base software 166 may identify, from the patient network historical database 164, information similar to information included in the received infusion pump patient database 216. The patient network historical database 164, for example, may include patient readings which are similar to readings included in the received infusion pump patient database 216.

In step 314, the patient network base software 166 may extract an algorithm from the historical database 164, wherein the algorithm may be associated with the similar database information. When the patient network base software 166 identifies similar information in the database 216, for example, the patient network base software 166 may extract an algorithm which is associated with such similar information in the database 216.

In step 316, the patient network base software 166 may compare the extracted algorithm with the pump algorithms 162 and identify a pump algorithm. The pump algorithm may be used to provide control information specific to a particular pump model or type. Whereas the extracted algorithm may provide control information based on a comparison of patient readings.

In step 318, the patient network base software 166 may extract one or more actions and/or one or more suggestions from the identified pump algorithm.

In step 320, the patient network base software 166 may transmit the one or more actions and/or the one or more suggestions to the MRI network 152.

In step 322, the patient network base software 166 may store the transmitted patient database 216 in the historical database 164.

Figure 4:
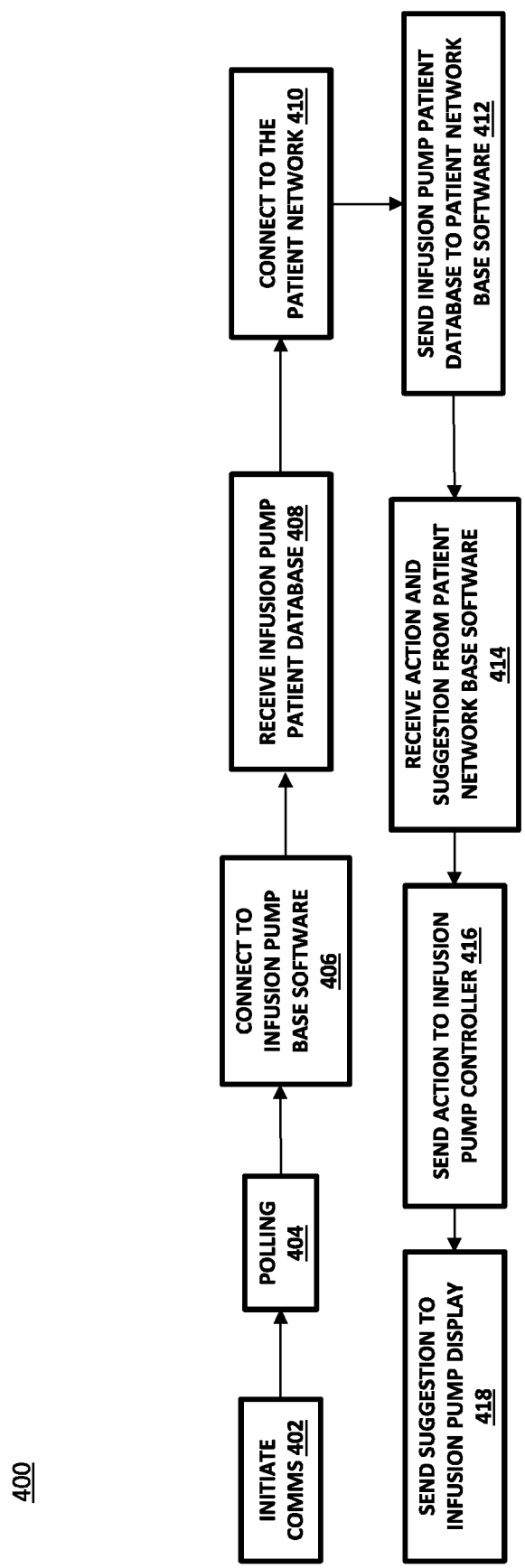
FIG. 4 is a flow diagram illustrating a method for providing infusion pump control information according to some embodiments of the present disclosure.

FIG. 4 is a flow diagram illustrating a method 400 for providing infusion pump control information. In step 402 of FIG. 4, the MRI network base software 154 may initiate communication. The MRI network base software 154 may initiate communication through various channels. The MRI network base software 154 may initiate communication through a communication interface. The communication interface may be included in the MRI network 152. The communication interface may communicate via the communication network 150.

In step 404, the MRI network base software 154 may continue polling for a connection with the infusion pump 210. The MRI network base software 154 may poll for a connection until a connection is established. The MRI network base software 154 may poll for a connection when a disconnection occurs between the MRI network base software 154 and the infusion pump 210.

In step 406, the MRI network base software 154 may connect to the infusion pump 210. The MRI network base software 154 may connect to the infusion pump 210 via the communication network 150.

In step 408, the MRI network base software 154 may receive, from the infusion pump 210, the infusion pump patient database 216. The infusion pump patient database 216 may be provided by the infusion pump base software 212.

In step 410, the MRI network base software 154 may connect to the patient network 160.

In step 412, the MRI network base software 154 may send the received infusion pump patient database 216 to the patient network 160. The MRI network base software 154 may transmit the database 216 via the communication interface 150. The patient network 160 may receive the transmitted database 216 using the patient network base software 166.

In step 414, the MRI network base software 154 may receive, from the patient network 160, one or more actions, one or more suggestions, or some combination thereof. Such actions and/or suggestions may be provided using the patient network base software 166.

In step 416, the MRI network base software 154 may transmit the one or more actions to the controller 218. In step 418, the MRI network base software 154 may transmit the one or more suggestions to the display 220.

FIGS. 5 and 6 illustrate embodiments of a data tables 502 and 602 stored in the patient network historical database 164. As shown, the data table 502 of FIG. 5 may include a patient identification column, a date column, a time column, a model column, a type column, a drug column, a blood oxygen saturation (SPO2%) column, a pulse column, a respiratory rate column, a temperature column, a blood pressure column, and an algorithm column. In other embodiments, more columns, or fewer columns, may be included. For example, as shown in FIG. 6, the data table 602 also includes columns identifying example actions that may be performed automatically and suggested actions are provided to the user. FIG. 6 also shows example algorithms that may be used to determine the actions and suggestions.

The patient network historical database 164 may include various patient data. The patient data may be captured from a plurality of patients while an MRI is in progress. Such patient data may include a patient identification; a date and a timestamp indicating when data was captured; a model number (or a model name) and type information identifying the machine used for the MRI, wherein the model number (or the model name) and type information may identify the infusion pump used for the MRI; a name of the drug used for the MRI; blood oxygen saturation data captured from the patient during the MRI; pulse data captured from the patient during the MRI; respiratory rate data captured from the patient during the MRI; body temperature data captured from the patient during the MRI; and blood pressure data captured from the patient during the MRI.

The patient network historical database 164 may also include an algorithm associated with the patient data. The algorithm may be associated with the patient data when the algorithm is selected by the patient network 160.

The patient network historical database 164 may be created using a plurality of infusion pump patient databases 216. The patient network historical database 164 may be updated to include additional infusion pump patient databases 216 when each of the additional infusion pump patient databases 216 is received.

Figure 7:
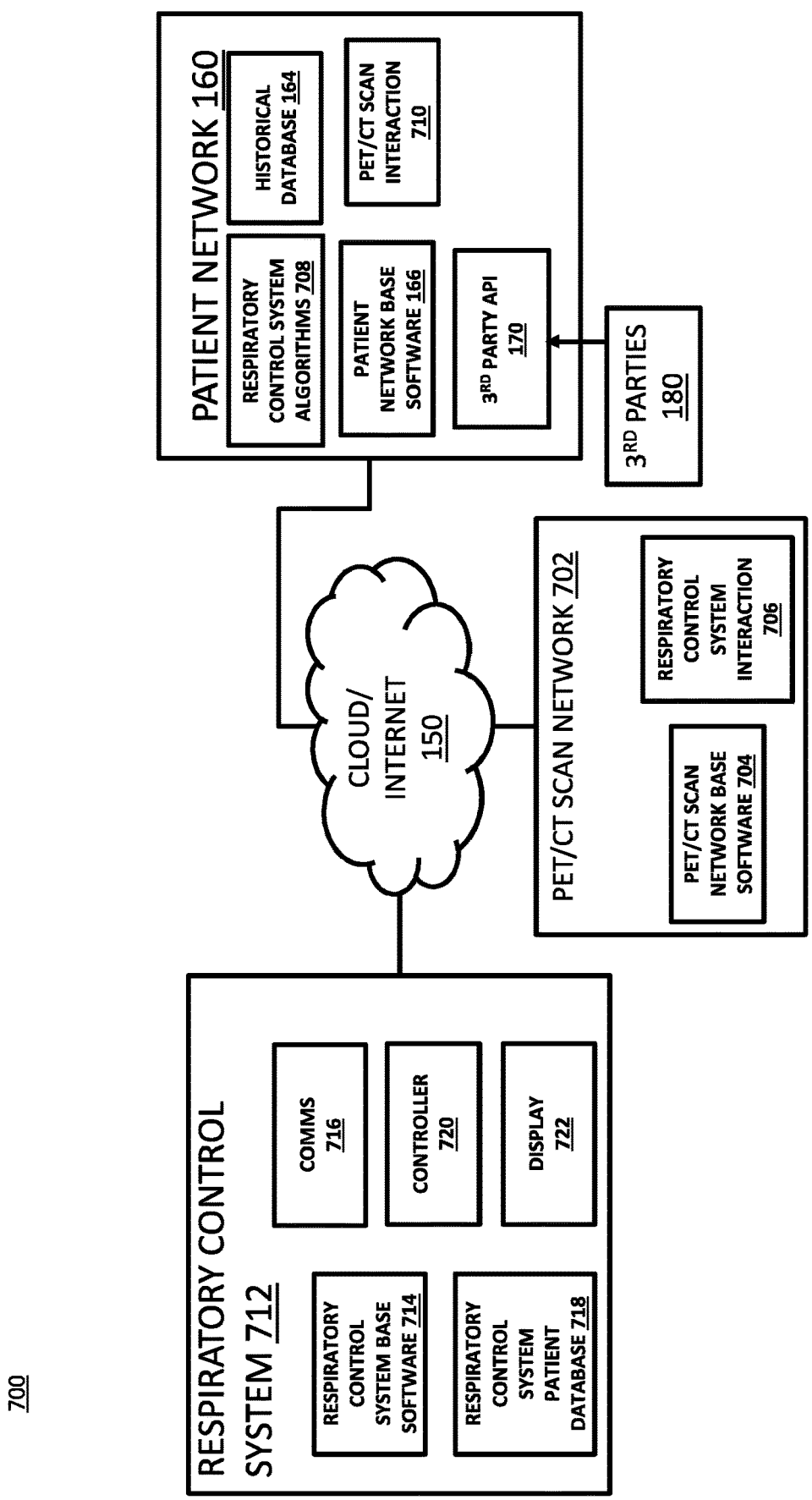
FIG. 7 shows an network environment for an exemplary PET/CT scan control system according to some embodiments of the present disclosure.
Figure 8:
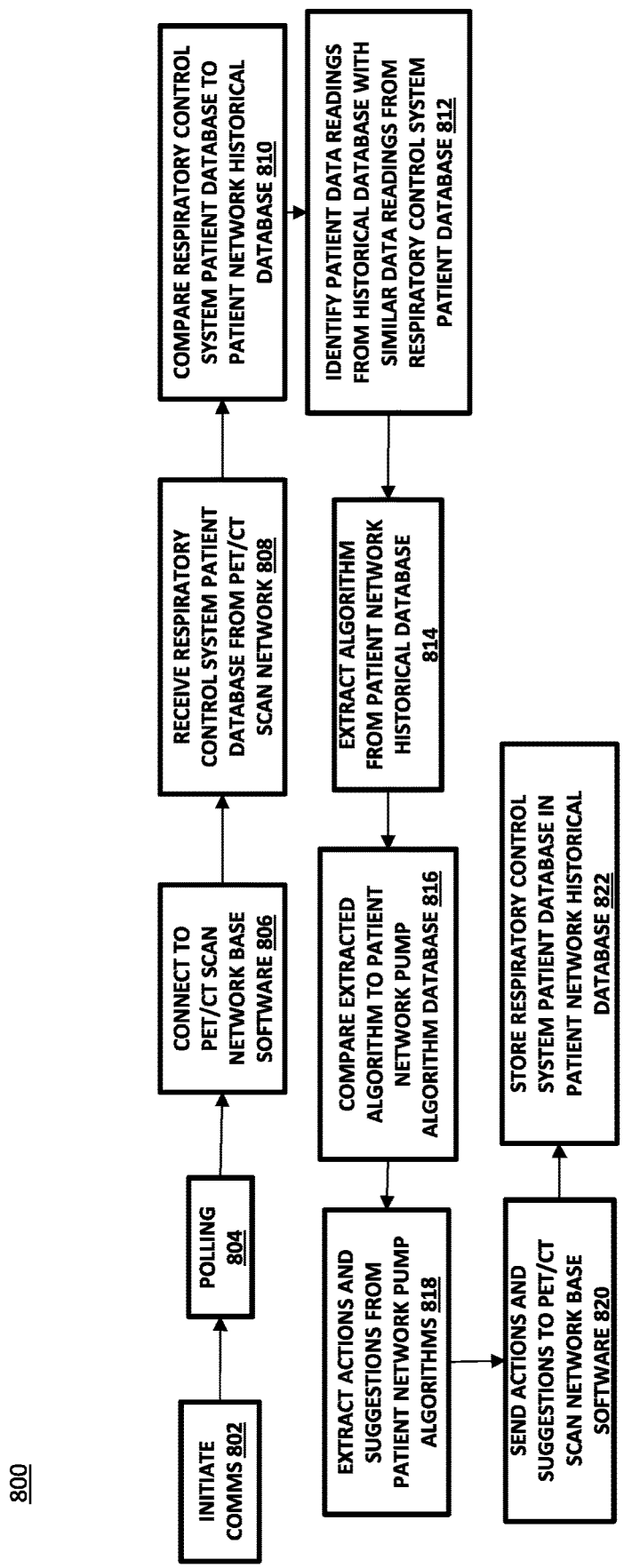
FIG. 8 is a flow diagram illustrating a method for identifying PET/CT scan control information according to some embodiments of the present disclosure.
Figure 9:
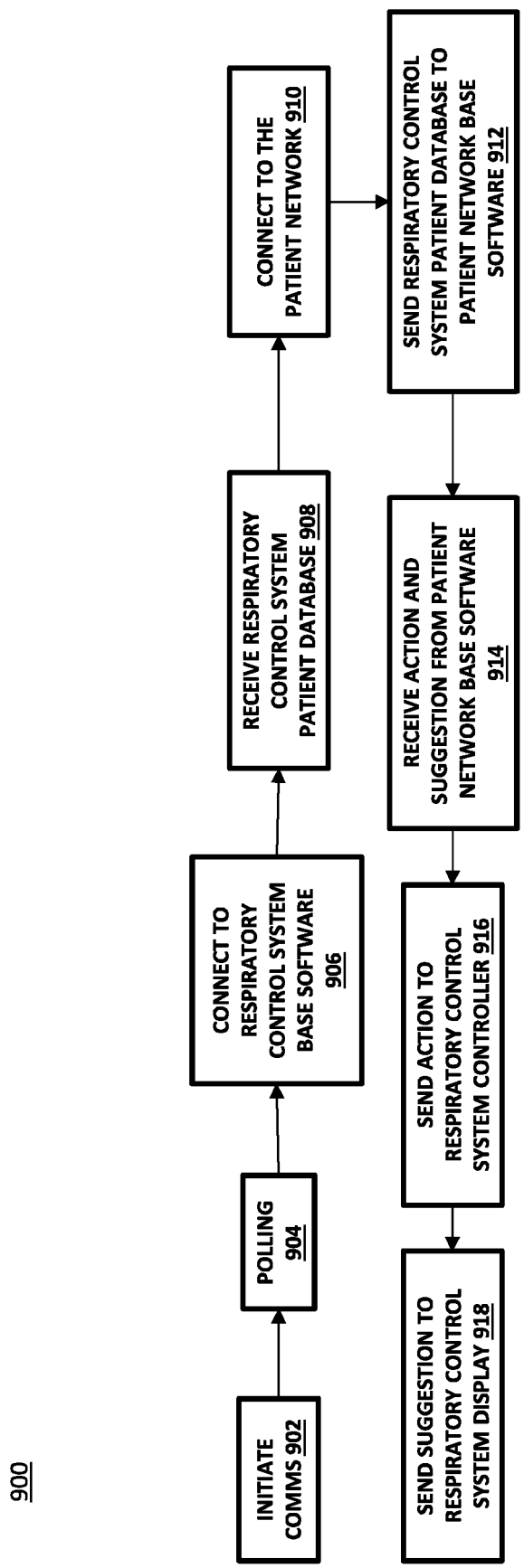
FIG. 9 is a flow diagram illustrating a method for providing PET/CT scan control information according to some embodiments of the present disclosure.

Referring now to FIGS. 7-9, the systems and methods of the present disclosure may also be used to control aspects of the imaging process for of the associated MRI systems and devices. By way of example and not limitation, a breath control system, such as the Interactive Breath Control System produced by Medspira LLC, may be used in combination with positron emission tomography (PET)/computed tomography (CT) scanners to correlate acquired images with specific portions of the respiratory cycle. This is desirable when acquiring images of a desired organ or tumor that may be distorted by abdominal shifting during portions of the respiratory cycle.

Currently caregivers and other practitioners must identify specific areas to scan when trying to locate an organ or tumor. By using the systems and methods of the present disclosure, with breath control systems and imaging systems, a collection of images taken during different portions of the respiratory cycle for a number of patients can be used to identify the ideal target locations for gathering images of the target organ/tumor. After use of the systems and methods disclosed herein, commands or other instructions may be generated to automatically control either the imaging devices (e.g. positioning and aim of the PET/CT scanner), automatically control breath systems to hold the patient in a specific portion of the respiratory cycle, or both. As such, the systems and methods of the present disclosure may be used to "hunt" for the target organ or tumor by identifying the location the target in similar patients. In various other embodiments, other patient interactive systems, imaging systems, or various combinations thereof may be used and controlled by the systems and methods of the present disclosure to correlate or sync time-variable patient parameters with acquired images.

FIG. 7, illustrates another environment 700 in which a method for adjusting PET/CT scan controls may be implemented. The environment 700 may include a respiratory control system 712, the communication network 150 (e.g., the cloud or Internet), the PET/CT scan network 702, the patient network 160, and the one or more third parties 180. The respiratory control system 712 may include respiratory control system base software 714, a communication interface 716, an respiratory control system patient database 718, a controller 720, and a display 722. The PET/CT scan network 702 may include the respiratory control system interaction 706. The PET/CT scan network 702 may also include an PET/CT scan network base software 704. The patient network 160 may include the one or more respiratory control system algorithms 708, the historical database 164, the third-party application program interface (API), and the PET/CT scan interaction 710. The patient network 160 may also include a patient network base software 166. The respiratory control system algorithms 708 may be stored in a respiratory control system algorithm database (not shown).

The respiratory control system 712 may record patient readings during an PET/CT scan and store the recorded readings in the database 718. The readings may be transmitted from the respiratory control system 712 to the PET/CT scan network 702. The readings may be transmitted via the communication network 150 using the communication interface 716. The transmitted readings may be transmitted from the PET/CT scan network 702 to the patient network 160. The readings may be compared, using the patient network base software 166, to the historical database 164 after the readings are transmitted to the patient network 160. The patient network base software 166 may identify readings from the database 164 which are similar to the transmitted readings. The patient network base software 166 may identify an algorithm associated with the similar readings. The algorithm may be associated with the similar readings in the database 164. The software 166 may compare the identified algorithm with the respiratory control system algorithms 708 to identify a respiratory control system algorithm. Actions and/or suggestions associated with the identified respiratory control system algorithm may be transmitted to the PET/CT scan network 702. The readings transmitted to the patient network 160 are also stored in the historical database 164. The identified algorithm may also be stored and associated with the transmitted readings in the database 164.

The transmitted actions may be transmitted to the controller 720. The transmitted suggestions may be transmitted to the display 722. The respiratory control system may use the actions and/or suggestions to control the respiratory control system. The respiratory control system may also use some but not all of the actions and/or suggestions. A technician controlling the respiratory control system, for example, may choose to implement some but not all of the actions and/or suggestions.

The one or more third parties 180 may access the patient network via the third party API 170. The one or more third parties 180 may be researchers and/or manufactures of PET/CT scan equipment. The third parties 180 may use the database 164 to improve algorithms and/or improve algorithms.

The patient network 160 may identify, for an respiratory control system 712, a model name and/or model type, based on the readings transmitted from the respiratory control system 712. The patient network 160 may use the model name and/or model type to select a respiratory control system algorithm from the one or more respiratory control system algorithms 708.

FIG. 8 is a flow diagram illustrating a method 800 for identifying PET/CT scan control information. In step 802, the patient network base software 166 may initiate communication. The patient network base software 166 may initiate communication through various channels. The patient network base software 166 may initiate communication through a communication interface. The communication interface may be included in the patient network 160. The communication interface may communicate via the communication network 150.

In step 804, the patient network base software 166 may continue polling for a connection with the PET/CT scan network 702. The patient network base software 166 may poll for a connection until a connection is established. The patient network base software 166 may poll for a connection when a disconnection occurs between the patient network base software 166 and the PET/CT scan network 702.

In step 806, the patient network base software 166 may connect to the PET/CT scan network 702. The patient network base software 166 may connect to the PET/CT scan network 702 via the communication network 150.

In step 808, the patient network base software 166 may receive, from the PET/CT scan network 702, the respiratory control system patient database 718. The respiratory control system patient database 718 may be provided to the patient network 160 by the PET/CT scan network base software 704. The PET/CT scan network 702 may provide the respiratory control system patient database 718 to the patient network 160 after receiving the database 718 from the respiratory control system 712.

In step 810, the patient network base software 166 may compare the received respiratory control system patient database 718 with the patient network historical database 164.

In step 812, the patient network base software 166 may identify, from the patient network historical database 164, information similar to information included in the received respiratory control system patient database 718. The patient network historical database 164, for example, may include patient readings which are similar to readings included in the received respiratory control system patient database 718.

In step 814, the patient network base software 166 may extract an algorithm from the historical database 164, wherein the algorithm may be associated with the similar database information. When the patient network base software 166 identifies similar information in the database 718, for example, the patient network base software 166 may extract an algorithm which is associated with such similar information in the database 718.

In step 816, the patient network base software 166 may compare the extracted algorithm with the respiratory control system algorithms 708 and identify a respiratory control system algorithm. The respiratory control system algorithm may be used to provide control information specific to a particular respiratory control system model or type. Whereas the extracted algorithm may provide control information based on a comparison of patient readings.

In step 818, the patient network base software 166 may extract one or more actions and/or one or more suggestions from the identified respiratory control system algorithm.

In step 820, the patient network base software 166 may transmit the one or more actions and/or the one or more suggestions to the PET/CT scan network 702.

In step 822, the patient network base software 166 may store the transmitted patient database 718 in the historical database 164.

FIG. 9 is a flow diagram illustrating a method 900 for providing PET/CT scan control information. In step 902, the PET/CT scan network base software 704 may initiate communication. The PET/CT scan network base software 704 may initiate communication through various channels. The PET/CT scan network base software 704 may initiate communication through a communication interface. The communication interface may be included in the PET/CT scan network 702. The communication interface may communicate via the communication network 150.

In step 904, the PET/CT scan network base software 704 may continue polling for a connection with the respiratory control system 712. The PET/CT scan network base software 704 may poll for a connection until a connection is established. The PET/CT scan network base software 704 may poll for a connection when a disconnection occurs between the PET/CT scan network base software 704 and the respiratory control system 712.

In step 906, the PET/CT scan network base software 704 may connect to the respiratory control system 712. The PET/CT scan network base software 704 may connect to the respiratory control system 712 via the communication network 150.

In step 908, the PET/CT scan network base software 704 may receive, from the respiratory control system 712, the respiratory control system patient database 718. The respiratory control system patient database 718 may be provided by the respiratory control system base software 714.

In step 910, the PET/CT scan network base software 704 may connect to the patient network 160.

In step 912, the PET/CT scan network base software 704 may send the received respiratory control system patient database 718 to the patient network 160. The PET/CT scan network base software 704 may transmit the database 718 via the communication interface 150. The patient network 160 may receive the transmitted database 718 using the patient network base software 166.

In step 914, the PET/CT scan network base software 704 may receive, from the patient network 160, one or more actions, one or more suggestions, or some combination thereof. Such actions and/or suggestions may be provided using the patient network base software 166.

In step 916, the PET/CT scan network base software 704 may transmit the one or more actions to the controller 720. In step 918, the PET/CT scan network base software 704 may transmit the one or more suggestions to the display 722.

Similar to the infusion pump of FIGS. 2-4, the respiratory control system of FIGS. 7-9 is a patient machine that interacts with a patient during an imaging procedure. As such, the systems and methods of the present disclosure may be used with other patient machines during other imaging procedures.

Figure 10:
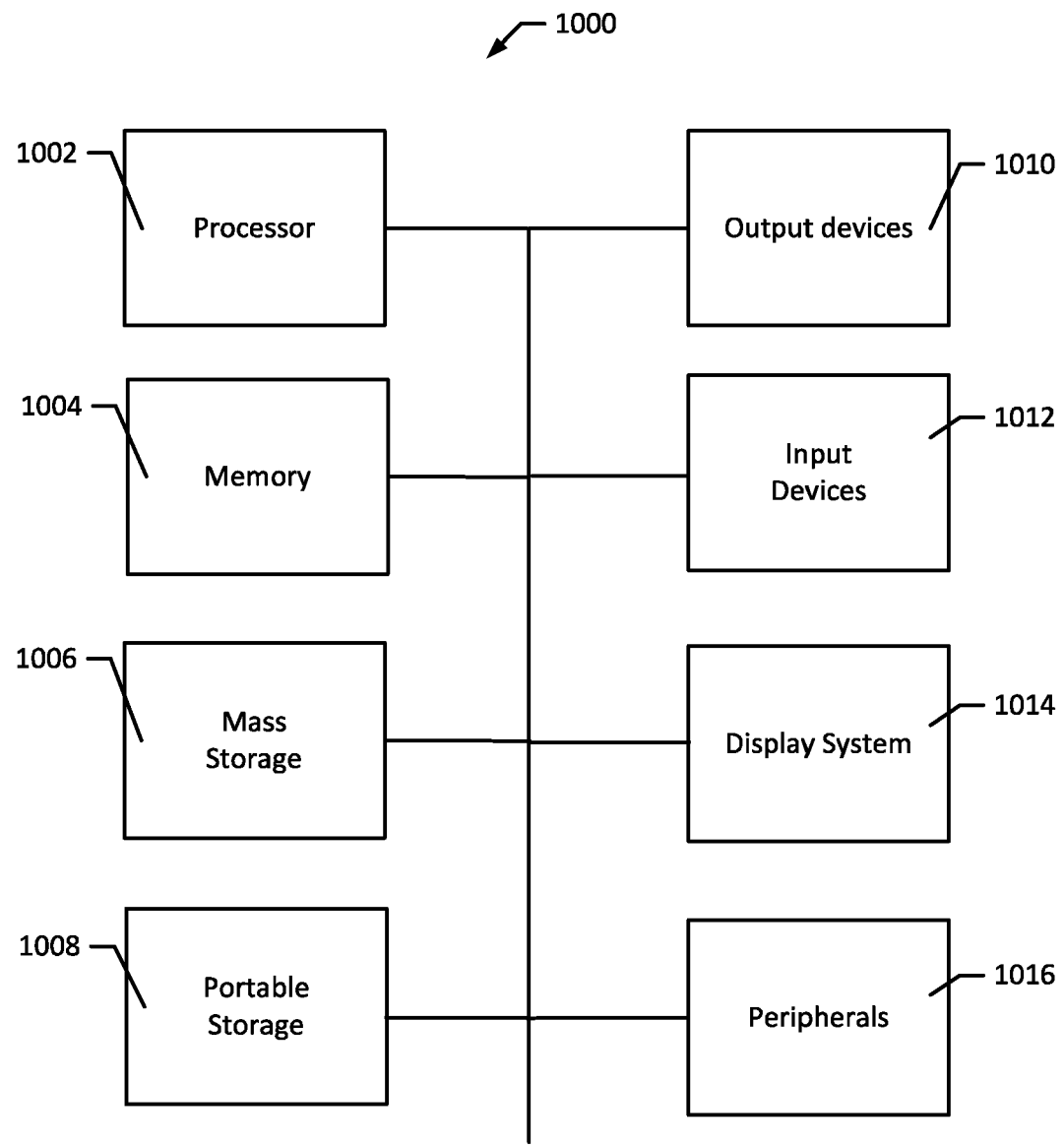
FIG. 10 illustrates an exemplary computing system that may be used to implement an embodiment of the present invention.

FIG. 10 illustrates an exemplary computing system 1000 that may be used to implement an embodiment of the present invention. The computing system of FIG. 10 includes one or more processors 1002 and memory 1004. Main memory 1004 stores, in part, instructions and data for execution by the processor 1002. Main memory 1004 can store the executable code when in operation. The system of FIG. 10 may further include a mass storage device 1006, portable storage medium drive(s) 1008, output devices 1010, user input devices 1012, a graphics display 1014, and peripheral devices 1016.

The components shown in FIG. 10 are depicted as being connected via a single bus 1018. However, the components may be connected through one or more data transport means. For example, the processor unit 1002 and main memory 1004 may be connected via a local microprocessor bus, and the mass storage device 1006, peripheral device(s) 1016, portable storage device 1008, and display system 1014 may be connected via one or more input/output (I/O) buses.

The mass storage device 1006, which may be implemented with a magnetic disk drive or an optical disk drive, is a non-volatile storage device for storing data and instructions for use by processor unit. The mass storage device 1006 can store the system software for implementing embodiments of the present invention and for purposes of loading that software into main memory 1004.

The portable storage device 1008 operates in conjunction with a portable non-volatile storage medium, such as a floppy disk, compact disk, or Digital video disc, to input and output data and code to and from the computer system of FIG. 10. The system software for implementing embodiments of the present invention may be stored on such a portable medium and input to the computer system via the portable storage device 1008.

Input devices 1012 provide a portion of a user interface. Input devices 1012 may include an alpha-numeric keypad, such as a keyboard, for inputting alpha-numeric and other information, or a pointing device, such as a mouse, a trackball, stylus, or cursor direction keys. Additionally, the system 1000 as shown in FIG. 10 includes output devices 1010. Examples of suitable output devices 1010 include speakers, printers, network interfaces, and monitors.

The display system 1014 may include a liquid crystal display (LCD) or other suitable display device. The display system 1014 receives textual and graphical information, and processes the information for output to the display device.

Peripherals 1016 may include any type of computer support device to add additional functionality to the computer system. For example, peripheral device(s) may include a modem or a router.

The components contained in the computer system 1000 of FIG. 10 are those typically found in computer systems that may be suitable for use with embodiments of the present invention and are intended to represent a broad category of such computer components that are well known in the art. Thus, the computer system 1000 of FIG. 10 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

The various computing devices 1000 disclosed herein include computer readable media (CRM) in memory 1004 on which the described applications and software are stored. The computer readable media may include volatile media, nonvolatile media, removable media, non-removable media, and/or another available medium that can be accessed by the processor 1002. By way of example and not limitation, the computer readable media comprises computer storage media and communication media. Computer storage media includes non-transitory storage memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system, both of which are hardware.

While various flow diagrams provided and described above may show a particular order of operations performed by certain embodiments of the invention, it should be understood that such order is exemplary (e.g., alternative embodiments can perform the operations in a different order, combine certain operations, overlap certain operations, etc.).

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for automatically identifying imaging system control information, the method comprising:

receiving patient data during an imaging procedure from a patient database associated with a patient machine, where the patient machine interacts with a patient of the imaging procedure;

and wherein the patient machine is an infusion pump or a respiratory control system;

comparing the received patient data to historical patient data stored in a historical database wherein the historical patient data includes patient data received during one or more other imaging procedures;

identifying, in the historical database, historical patient data that is similar to the received patient data;

extracting, from the historical database, an algorithm for the imaging system, wherein the algorithm is associated with the identified historical patient data similar to the received patient data;

using the algorithm to identify control information for the imaging system; and transmitting the identified control information to an imaging machine.

2. The method of claim 1, further comprising:

polling the imaging system for the imaging machine; and automatically connecting to the imaging machine.

3. The method of claim 1, wherein comparing the received patient data to historical patient data further comprises identifying particular historical patient data that is similar to the received data.

4. The method of claim 1, further comprising:

retrieving the algorithm data from the historical database; and comparing the identified algorithm to a patient machine algorithm associated with the patient machine.

5. The method of claim 1, further comprising storing the identified control information data in the historical database.

6. A system for automatically identifying imaging system control information, the system comprising:

a patient machine comprising a patient machine database, wherein the patient machine is an infusion pump or a respiratory control system;

an imaging system comprising an imaging machine; and a patient network computing device, comprising a memory, a processor, and a historical database; the processor to:

receive patient data during an imaging procedure from the patient machine database;

compare the received patient data to historical patient data stored in the historical database, wherein the historical patient data includes patient data received during one or more other imaging procedures; identify, in the historical database, historical patient data that is similar to the received patient data;

extract, from the historical database, an algorithm for the imaging system, wherein the algorithm is associated with the identified historical patient data similar to the received patient data;

use the algorithm to identify control information for the imaging system; and transmit the identified control information to the imaging machine.

7. The system of claim 6, further comprising the processor to:

poll the imaging system for the imaging machine; and automatically connect to the imaging machine.

8. The system of claim 6, wherein comparing the received patient data to historical patient data further comprises identifying particular historical patient data that is similar to the received patient data.

9. The system of claim 6, further comprising the processor to:

retrieve the algorithm data from the historical database; and compare the identified algorithm to a patient machine algorithm associated with the patient machine.

10. The system of claim 6, further comprising the processor to store the identified control information data in the historical database.

* * * * *